United States Patent
Kuhlmann et al.

(10) Patent No.: US 7,038,773 B2
(45) Date of Patent: May 2, 2006

(54) APPARATUS AND METHODS FOR ENABLING ROBUST SEPARATION BETWEEN SIGNALS OF INTEREST AND NOISE

(75) Inventors: Lionel Kuhlmann, Charlottenlund (DK); Jianbo Gao, Sunnyvale, CA (US); Mark C. Sweeney, San Jose, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

(21) Appl. No.: 10/848,631

(22) Filed: May 18, 2004

(65) Prior Publication Data
US 2004/0235206 A1 Nov. 25, 2004

Related U.S. Application Data

(60) Provisional application No. 60/472,032, filed on May 19, 2003.

(51) Int. Cl.
*G01N 21/00* (2006.01)
*G01B 11/30* (2006.01)

(52) U.S. Cl. ............... 356/237.4; 356/600; 356/394
(58) Field of Classification Search .. 356/237.1–237.5, 356/600, 394, 445–448; 382/141, 168, 107; 348/125, 128, 126
See application file for complete search history.

(56) References Cited

U.S. PATENT DOCUMENTS

| | | | | |
|---|---|---|---|---|
| 5,416,594 A | * | 5/1995 | Gross et al. | 356/237.5 |
| 6,201,601 B1 | * | 3/2001 | Vaez-Iravani et al. | 356/237.4 |
| 6,266,138 B1 | * | 7/2001 | Keshavmurthy | 356/237.2 |
| 6,515,742 B1 | * | 2/2003 | Ruprecht | 356/237.4 |
| 6,529,270 B1 | * | 3/2003 | Bills | 356/237.2 |
| 6,538,730 B1 | * | 3/2003 | Vaez-Iravani et al. | 356/237.2 |
| 6,606,153 B1 | * | 8/2003 | Marxer et al. | 356/237.3 |
| 6,633,372 B1 | * | 10/2003 | Voinalovich | 356/73 |

* cited by examiner

*Primary Examiner*—Hoa Q. Pham
(74) *Attorney, Agent, or Firm*—Beyer Weaver & Thomas, LLP (57) ABSTRACT

Disclosed are methods and apparatus for analyzing the Raze data provided by an optical inspection tool. The Haze data is analyzed so as to detect defects associated with the specimen surface. In general, the Haze data is first conditioned so that background noise which corresponds to low frequency variation on the specimen is separated or removed from the Haze data prior to analysis of such Haze data. In a specific embodiment, low frequency variations in the specimen surface are characterized, in effect, as an optical surface upon which an incident beam is directed. The Haze data that conforms to this resulting polynomial equation is then subtracted from the original Haze data to result in residual data, where slow variations in surface roughness are subtracted out, leaving possible defect information in the residual Haze data. This residual Haze data may then be analyzed to determine whether the specimen contains a defect.

58 Claims, 8 Drawing Sheets

| i | n | l | RMS Coeff | Zernike Polynomial term | Zernike Monomial | Meaning |
|---|---|---|---|---|---|---|
| 1 | 0 | 0 | 1 | 1 | 1 | Bias |
| 2 | 1 | 1 | 2 | $\rho \sin(\theta)$ | Y | Tilt y direction |
| 3 | 1 | -1 | 2 | $\rho \cos(\theta)$ | X | Tilt x direction |
| 4 | 2 | 2 | $\sqrt{6}$ | $\rho^2 \sin(2\theta)$ | 2XY | Astigmatism 1st ord. 45° |
| 5 | 2 | 0 | $\sqrt{3}$ | $(-1+2\rho^2)$ | $(-1+2X^2+2Y^2)$ | Defocus |
| 6 | 2 | -2 | $\sqrt{6}$ | $\rho^2 \cos(2\theta)$ | $-Y^2+X^2$ | Astigmatism 1st ord. 0° |
| 7 | 3 | 3 | $2\sqrt{2}$ | $\rho^3 \sin(3\theta)$ | $(-Y^3+3YX^2)$ | Trifoil 30° |
| 8 | 3 | 1 | $2\sqrt{2}$ | $(-2\rho+3\rho^3)\sin(\theta)$ | $(-2Y+3Y^3+3YX^2)$ | Coma y direction |
| 9 | 3 | -1 | $2\sqrt{2}$ | $(-2\rho+3\rho^3)\cos(\theta)$ | $(-2X+3Y^2X+3X^3)$ | Coma x direction |
| 10 | 3 | -3 | $2\sqrt{2}$ | $\rho^3 \cos(3\theta)$ | $(-3*YY.*X+(X,3))$ | Trifoil 0° |
| 11 | 4 | 4 | $\sqrt{10}$ | $\rho^4 \sin(4\theta)$ | $(-4Y^3X+4YX^3)$ | Tetrafoil 22.5° |
| 12 | 4 | 2 | $\sqrt{10}$ | $(-3\rho^2+4\rho^4)\sin(2\theta)$ | $(-6YX+8Y^3X+8YX^3)$ | Astigmatism 2nd ord. 45° |
| 13 | 4 | 0 | $\sqrt{5}$ | $(1-6\rho^2+6\rho^4)$ | $(1-6*Y^2+6Y^4-6X^2+12Y^2X^2+6X^4)$ | Spherical aberration |
| 14 | 4 | -2 | $\sqrt{10}$ | $(-3\rho^2+4\rho^4)\cos(2\theta)$ | $(3Y^2-4Y^4-3*X^2+4X^4)$ | Astigmatism 2nd ord. 0° |
| 15 | 4 | -4 | $\sqrt{10}$ | $\rho^4 \cos(4\theta)$ | $(Y^4-6Y^2*X^2+X^4)$ | Tetrafoil 0° |

APPARATUS AND METHODS FOR ENABLING ROBUST SEPARATION BETWEEN SIGNALS OF INTEREST AND NOISE

CROSS REFERENCE TO RELATED PATENT APPLICATION

This application claims priority of U.S. Provisional Patent Application No. 60/472,032, entitled APPARATUS AND METHODS FOR ENABLING ROBUST SEPARATION BETWEEN SIGNALS OF INTEREST AND NOISE, filed 19 May 2003 by Lionel Kuhlmann, et al. which application is incorporated herein by reference in its entirety for all purposes.

BACKGROUND OF THE INVENTION

The present invention relates generally to inspection of specimens, such as semiconductor specimens. More specifically, it relates to the analysis of Haze data collected during inspection of bare wafers or wafers that have a uniform film, and the like.

Generally, the industry of semiconductor manufacturing involves highly complex techniques for fabricating integrating circuits using semiconductor materials which are layered and patterned onto a substrate, such as silicon. Due to the large scale of circuit integration and the decreasing size of semiconductor devices, the substrate must be defect free prior to fabrication of the integrated circuits. Thus, inspection procedures for detecting defects, such as particles or scratches, on the bare substrate are therefore critical to maintain quality control. Since the inspection procedures are an integral and significant part of the manufacturing process, the semiconductor industry is constantly seeking to improve the accuracy and efficiency of inspection procedures.

One conventional optical inspection tool for locating defects on bare or unpatterned wafers work by scanning the surface of the bare wafer with a tightly focused laser spot and measuring the amount of light scattered by the illuminated spot on the wafer. One example of such an inspection tool is the Surfscan SP1 DLS and TBI tool available from KLA-Tencor, Inc. of San Jose, Calif.

The incident light may be scattered by defects, such as particles. Thus, one may detect defects by analyzing the light scattered and reflected by the specimen and defects located on the specimen. In addition to gross defects, the surface texture itself produces a certain amount of diffracted light in addition to the light scattered by particle defects. This surface light scatter, commonly referred to as Haze, tends to be concentrated at smaller angles near the specularly reflected light beam. The Haze signal may be analyzed to determine surface roughness. Haze is generally defined as a decrease in the smoothness of a wafer surface from the ideal due to imperfections in the surface, such as, minute steps, contaminants in the grain structure, and other surface defects which cause light scattering or absorption. Subjectively, a wafer surface with a high amount of Haze appears dull while a wafer with little Haze appears glossy. One can then visually inspect the Haze image and generally assess the surface roughness profile.

Although conventional systems for detecting defects work well in certain applications, there is a continuing need for improved inspection apparatus and techniques for facilitating defect detection on bare specimens or specimens having a uniform film layer or stack.

SUMMARY OF THE INVENTION

Accordingly, mechanisms are provided for analyzing the Haze data provided by an optical inspection tool. The Haze data is analyzed so as to detect defects associated with the specimen surface. In general, the Haze data is first conditioned so that background noise which corresponds to low frequency variation on the specimen is separated or removed from the Haze data prior to analysis of such Haze data. In a specific embodiment, low frequency variations in the specimen surface are characterized, in effect, as an optical surface upon which an incident beam is directed. In one example, the Haze data that corresponds to the specimen surface is characterized with a polynomial equation, such as a Zernike equation. In other words, a polynomial equation is fit to the low frequency or background noise (or variation) of the Haze data. The Haze data that conforms to this resulting polynomial equation is then subtracted from the original Haze data to result in residual data, where slow variations in surface roughness are subtracted out, leaving possible defect information in the residual Haze data. This residual Haze data may then be analyzed to determine whether the specimen contains a defect. Techniques for enhancing detection of defects by analyzing the residual data are also disclosed. Preferably, techniques for calibrating the resulting residual data so that it is normalized between different inspection tools are also provided.

One useful application of these inventive techniques is to use the Haze analysis results to monitor a processing tool, such as a polishing tool which is used to polish the bare specimen or a uniform film of the specimen. For example, when the polishing pad becomes worn, this wear will affect the Haze data collected from the polished specimens. For instance, variations in the Haze data collected from wafers that were polished by the worn polishing pad may be processed and analyzed so as to determine that the polishing pad is worn. Additionally, in embodiments which include calibration of the residual data so that it is normalized across different inspection tools, the residual data can more accurately and reliably be assessed for deviations which correspond to polishing pad wear, as well as other processing tool problems.

In a specific embodiment, a method of analyzing Haze data provided from a surface of a specimen (e.g., a bare semiconductor wafer or a specimen having a uniform film disposed thereon) is disclosed. Haze data which corresponds to a surface roughness of the specimen is provided. Low frequency variations are then removed from the Haze data to form residual data that corresponds to any defects which are present in the surface of the specimen. In a further embodiment, the residual data is analyzed to determine whether the specimen has any defects.

In a specific implementation, removing low frequency variations from the Haze data is accomplished by fitting the low frequency variations of the Haze data to a fitting plan and subtracting the fitting plan from the Haze data to form the residual data. In a further aspect, the fitting plan is in the form of a two dimensional (2D) polynomial equation. In yet another aspect, the 2D polynomial equation is a Zernike polynomial. In a specific example, Zernike polynomial includes terms for tilt direction, tilt magnitude, and bowl shape. In a further embodiment, the Zernike polynomial has an order greater than 2. In another embodiment, the Zernike polynomial has an order less than 9. In an alternative embodiment, the low frequency variations are removed from the Haze data is accomplished using a filter.

In further aspect, the Haze data is pre-processed to exclude a portion of the Haze data from the fitting plan. In one specific implementation, the pre-processing includes excluding outliers within the Haze data from the fitting plan, and the outliers include intensity values which correspond to the specimen's edge and large blob defects. In a further example, excluding outliers includes determining a mean and standard deviation for the Haze data, determining a threshold which depends on the mean and standard deviation, and excluding Haze data which falls below the threshold from the fitting plan. In a specific embodiment, the threshold is set equal to the mean plus a predetermined factor multiplied by the standard deviation. In another embodiment, the predetermined factor is set equal to 1.5. In another aspect, the predetermined factor is determined experimentally.

In a specific implementation, the residual data is analyzed by a) obtaining a window which contains a portion of the residual data; b) determining a minimum pixel having a lowest intensity and a maximum pixel having a maximum intensity within the obtained window; and c) determining whether the window has a defect based on the minimum pixel, the maximum pixel, and a predetermined threshold. In a first technique, when the minimum pixel minus the maximum pixel is greater than the predetermined threshold, it is determined that the window has a defect. In a second step, when a maximum of (A) a center pixel of the window minus the minimum pixel and (B) the maximum pixel minus the center pixel is greater than the predetermined threshold, it is determined that the window has a defect. Steps (a) through (c) may be repeated for a plurality of windows which contain other areas of the residual data so that all portions of the residual data are analyzed.

In another specific embodiment, the predetermined threshold is determined by determining a histogram based on the residual data; selecting a range of residual values from the residual data; and determining a threshold based on the selected range. In one aspect, the threshold is determined by multiplying a predetermined factor times the range, wherein the predetermined factor varies for each system which provides Haze data so that the threshold is normalized between the different systems. In another aspect, the threshold is determined by multiplying a factor times the range plus an absolute threshold value. In another example, the selected range is between about 5 and 95 percent.

In another aspect, the invention pertains to a computer system operable to analyze Haze data provided from a surface of a specimen. The computer system includes one or more processors and one or more memory configured to perform one or more of the above method operations. In yet another aspect, the invention pertains to a computer program product for analyzing Haze data provided from a surface of a specimen. The computer program product includes at least one computer readable medium and computer program instructions stored within the at least one computer readable product configured to perform one or more of the above described inventive procedures.

These and other features and advantages of the present invention will be presented in more detail in the following specification of the invention and the accompanying figures which illustrate by way of example the principles of the invention.

DETAILED DESCRIPTION OF SPECIFIC EMBODIMENTS

Reference will now be made in detail to a specific embodiment of the invention. An example of this embodiment is illustrated in the accompanying drawings. While the invention will be described in conjunction with this specific embodiment, it will be understood that it is not intended to limit the invention to one embodiment. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

In general terms, the present invention provides techniques and apparatus for analyzing Haze data obtained from a bare specimen or a specimen having one or more uniform films. Although the present invention is mainly described below as being applied to bare semiconductor wafers, it may be applied to other types of specimens which consist of a bare substrate or have a uniform film or film stack deposited thereon. Prior to analysis of the Haze data, the Haze data is first filtered so as to eliminate background noise, such as low frequency variations across the specimen or wafer.

Background noise is generally defined as intensity values which correspond to a specimen's global roughness as it slowly varies across the specimen. Background noise does not include variations which typically correspond to defects, such as scratches, pits, trenches, bumps, dimples, polishing defects, etc. in the sample's surface For instance, the Haze data may include background noise in the form of intensity values having a "bowl-shape" profile across the wafer, where the intensity values rise at the wafer edges and drop in values towards the center of the wafer. Other examples of background noise include any combination of the following: a uniform roughness of the specimen surface, an angled plane of the specimen surface, and higher order roughness variations of the specimen surface.

After the background noise is subtracted or filtered from the Haze data, the residual Haze data may then be analyzed to detect defects or high frequency variations across the specimen. Defects may include scratches, pits, trenches, bumps, dimples, and polishing defects in the sample surface. Techniques and apparatus for effectively analyzing the Haze data for defects are also provided and described further below.

Figure 1A:
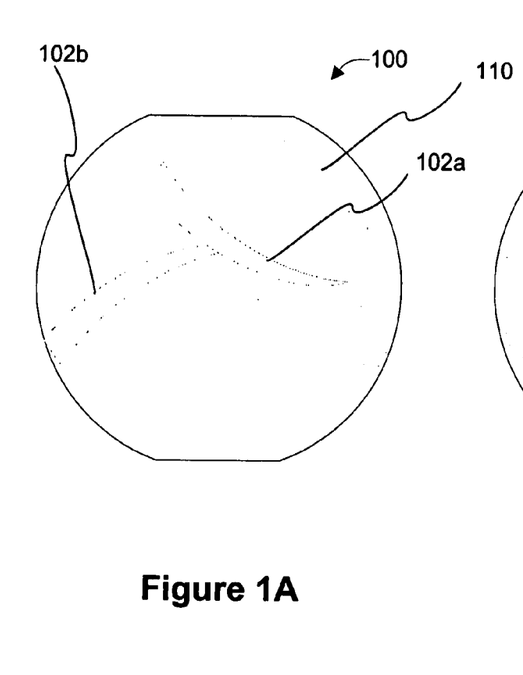
FIG. 1A is diagrammatic representation of Haze data as collected from a bare semiconductor wafer.
Figure 1B:
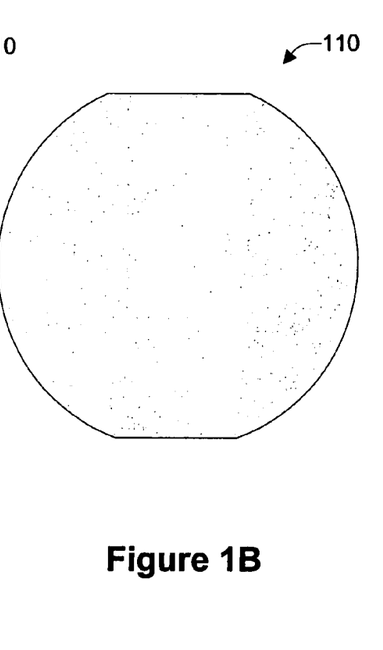
FIG. 1B is a diagrammatic representation of a fitting result as applied to the background noise of the Haze data of FIG. 1A in accordance with one embodiment of the present invention.
Figure 1C:
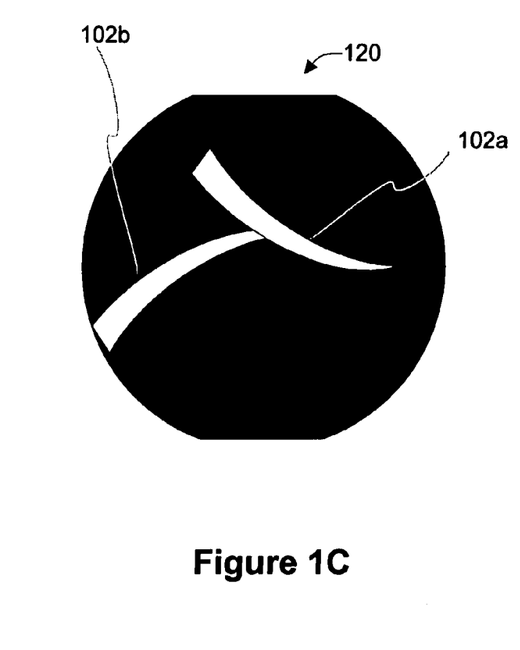
FIG. 1C is a diagrammatic representation of residual data which results from subtracting the fitting results of FIG. 1B from the Haze data of FIG. 1A in accordance with one embodiment of the present invention.

FIGS. 1A through 1C generally illustrate techniques for conditioning and analyzing Haze data in accordance with one embodiment of the present invention. FIG. 1A is diagrammatic representation of Haze data 100 from a bare wafer as output from an inspection system for inspecting substrates which is also configured to provide such Haze data. A system which is capable of providing Haze data is the Surfscan SP1 DLS tool available from KLA-Tencor, Inc. of San Jose, Calif. Haze is generally proportional to a specimen's surface roughness and the refraction index of one or more films deposited on the specimen (if present).

As shown, the Haze data includes background noise 110 and two large scratch type defects 102a and 102b. The scratch type defects are exaggerated to better illustrate the techniques of the present invention. The two large scratch defects 102 may difficult to detect in the presence of the background noise 110. That is, the scratches 102 may be difficult to distinguish from the background noise 110.

FIG. 1B is a diagrammatic representation of a fitting result 110 as applied to the Haze data's background noise in accordance with one embodiment of the present invention. As shown, the fitting result corresponds to only the background noise 110 of FIG. 1A. FIG. 1C is a diagrammatic representation of defect results or residual data 120 after subtracting the fitting results 110 of FIG. 1B from the Haze data 100 of FIG. 1A in accordance with one embodiment of the present invention. As shown, only the scratches 102a and 102b of FIG. 1A are present within the residual data 120 of FIG. 1C.

Figure 2:
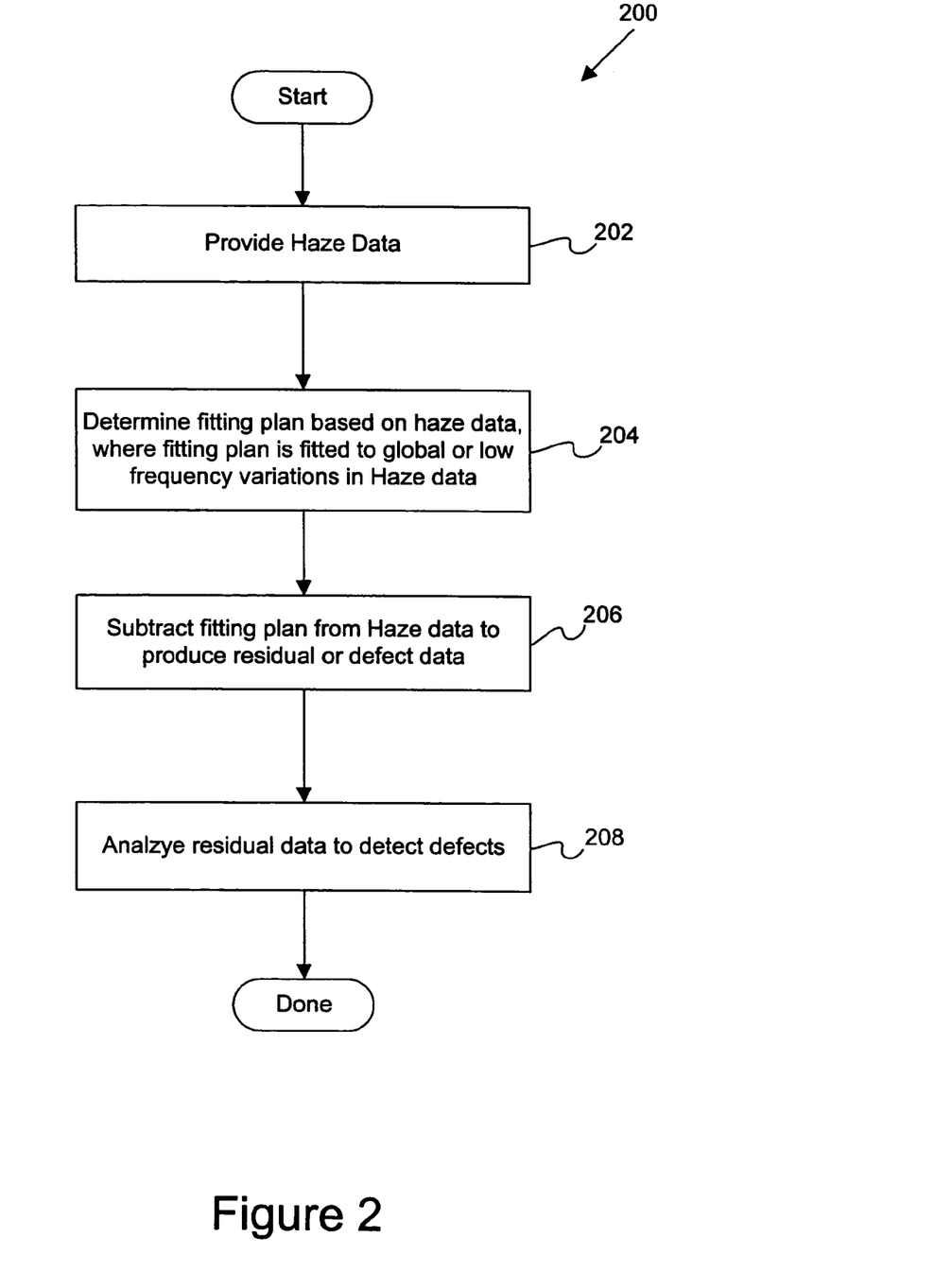
FIG. 2 is a flow chart illustrating a procedure for analyzing Haze data in accordance with one embodiment of the present invention.

FIG. 2 is a flow chart illustrating a procedure 200 for analyzing Haze data in accordance with one embodiment of the present invention. Initially, Haze data is provided in operation 202. A fitting plan based on the Haze data is then determined in operation 204. This fitting plan is fitted to the global or low frequency variation (referred herein as "background noise") of the Haze data. The fitting plan is then subtracted from the Haze data to produce residual or defect data in operation 206. The residual data is the analyzed to detect defects in operation 208. The procedure for analyzing the Haze data then completes.

The Haze data may be provided in any suitable manner. Systems for inspecting bare wafers may typically provide such Haze data. One example system is the Surfscan SP1 DLS tool available from KLA-Tencor, Inc. of San Jose, Calif. The fitting plan generally conforms to the global or low frequency variations within the Haze data. For example, any two dimensional polynomial may be utilized for the fitting plan. Alternatively, the Haze data may be filtered through any filtering mechanism. Zernike polynomials are well known within the optics industry and broadly used functions for describing the wave front of optical systems in terms of aberrations. In the present invention, Zernike polynomial may be applied to the Haze data so that the surface is characterized as an optical surface.

The Zernike polynomials are a set of orthogonal polynomials that arise in the expansion of a wave front function for optical systems with circular pupils. The odd and even Zernike polynomials are given by $$\begin{cases} {}^{o}U_n^m(\rho, \phi) = R_n^m(\rho)\sin(m\phi) \\ {}^{e}U_n^m(\rho, \phi) = R_n^m(\rho)\cos(m\phi), \end{cases} \quad (1)$$

where the radial function $R_n^m(\rho)$ is defined for n and m integers with $n \geq m \geq 0$ by $$R_n^m(\rho) = \quad (2)$$

$$\begin{cases} \sum_{l=0}^{(n-m)/2} \frac{(-1)^l(n-l)!}{l!\left[\frac{1}{2}(n+m)-l\right]!\left[\frac{1}{2}(n-m)-l\right]!}\rho^{n-2l} & \text{for } n-m \text{ even} \\ 0 & \text{for } n-m \text{ odd.} \end{cases}$$

Here, $\phi$ is the azimuthal angle with $0 \leq \phi \leq 2\pi$ and $\rho$ is the radial distance with $0 \leq \rho \leq 1$.

Any arbitrary radial function $F(\rho,\phi)$ can be represented in terms of Zernike polynomials as $$F(\rho, \phi) = \sum_{m=0}^{\infty} \sum_{n=m}^{\infty} [A_n^m \, {}^oU_n^m(\rho, \phi) + B_n^m \, {}^eU_n^m(\rho, \phi)] \quad (3)$$

The coefficients $A_n^m$ and $B_n^m$ in the above expansion are the Zernike fitting coefficients which can be calculated by $$\begin{cases} A_n^m = \frac{(n+1)}{\varepsilon_{mn}^2 \pi} \int_0^1 \int_0^{2\pi} F(\rho, \phi) \, {}^oU_n^m(\rho, \phi)\rho \, d\phi \, d\rho, \\ B_n^m = \frac{(n+1)}{\varepsilon_{mn}^2 \pi} \int_0^1 \int_0^{2\pi} F(\rho, \phi) \, {}^eU_n^m(\rho, \phi)\rho \, d\phi \, d\rho, \end{cases} \quad (4)$$

where $$\varepsilon_{mn} = \begin{cases} \frac{1}{\sqrt{2}} & \text{for } m = 0, n \neq 0 \\ 1 & \text{otherwise} \end{cases}$$

Figure 3A:
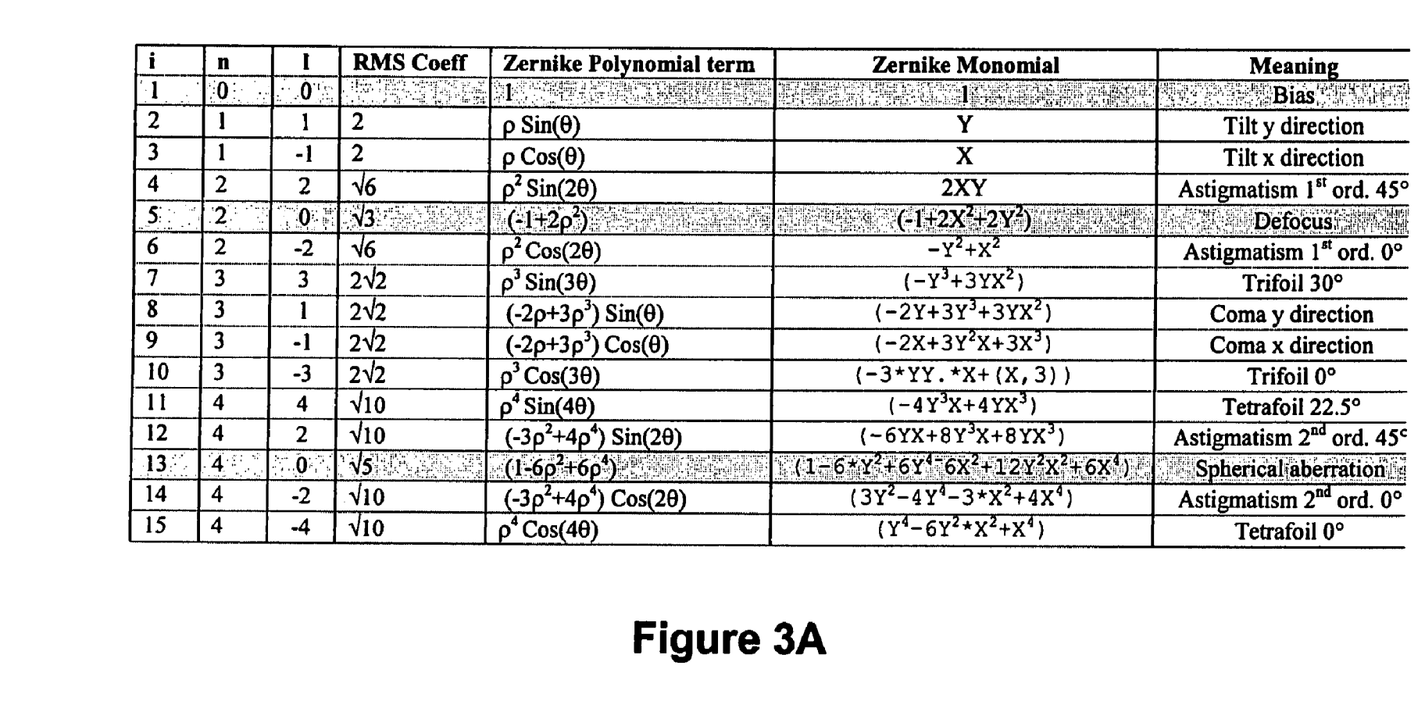
FIG. 3A is a table that may used to determine the number of terms of a Zernike polynomial fitting plan when the order of the Zernike fitting is specified in accordance with one embodiment of the present invention.

A Zernike fitting algorithm is well suited for applying to a wafer surface due to its circular nature. Once the order of the Zernike fitting is specified, the number of terms can be calculated by the table of FIG. 3A. A special case is the order 0, where no fitting is performed. The default value for the order is 3 although other term numbers may be used depending on the particular application. In the analysis, the tilt direction, tilt magnitude, and bowl shape are preferably included for fitting to the Haze data. These terms are defined as follows;

Tilt_Drection=$a \tan(z(2), z(1))$;

Tilt_Magnitude=sqrt($z(2)*z(2)+z(1)*z(1)$); and

Bowl_Shape=$z(4)$.

Z(i), where i equals 0,1,2,3,4, . . . , are Zernike fitting coefficients. An order greater than or equal to 2 may be used to calculate all three parameters. Otherwise, the order is less than 9. The following factors may be considered for selecting the order: good fit, memory usage, and throughput.

Since the Haze values at the specimen or wafer edge (as well as any defects) tend to have very high intensity values, these data points may not be used for the fitting because they would otherwise bias the fitting results. That is, when a fitting result which includes such edge values and blob defect values is subtracted from the Haze data, it may inadvertently subtract out the actual blob defects. Accordingly, the Haze data is preferably pre-processed before the fitting plan is estimated and applied to the Haze data. This pre-processing excludes the "Bad" Haze pixel data or outliers from the fitting plan. Typically, these outliers will be in the form of edge pixel and large blob defects. These outliers may generally include any large defects or imperfections creating large absolute values as well as high local Haze gradients.

Figure 3B:
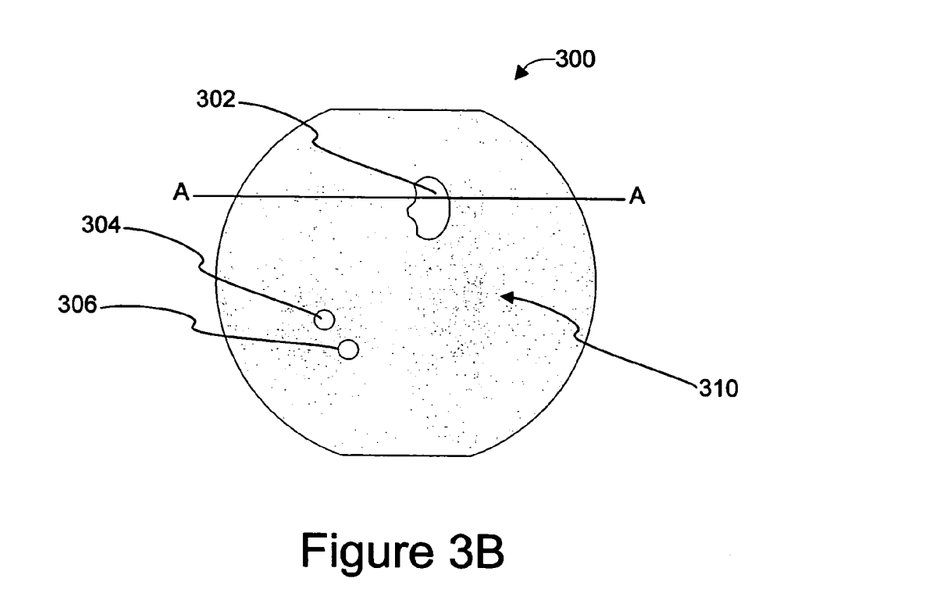
FIG. 3B is a diagrammatic representation of Haze data which includes background noise and three large blob defects.
Figure 3C:
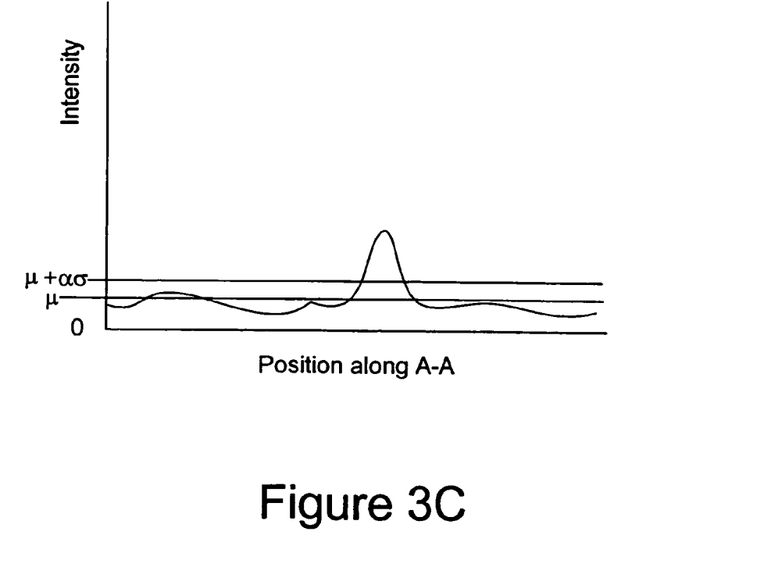
FIG. 3C is a graph showing intensity values as a function of a position along cross section A—A of FIG. 3B in accordance with one embodiment of the present invention.

FIG. 3B is a diagrammatic representation of Haze data 300 which includes background noise 310 and three large blob defects 302, 304, and 306. The background noise 310 has a generally gray appearance, while the three large blobs 302, 304, and 306 have a high intensity or bright appearance. FIG. 3C is a graph showing intensity values as a function of a position along cross section A—A of FIG. 3B in accordance with one embodiment of the present invention. For a robust fitting, a mean and standard deviation of the Haze intensity data may first be determined. The standard deviation $\sigma$ is then multiplied by a factor $\alpha$ and added to the mean $\mu$ to determine a threshold for excluding a portion of the Haze data.

The factor $\alpha$ may be determined a number of ways. For example, a first default $\alpha$ may be selected and applied to samples having known defects. The factor $\alpha$ is then adjusted until the defects are not excluded from the Haze data after the fitting plan is subtracted. The fitting plan may be based on a portion of the smaller defects or none of the defects. A $\alpha$ value of 1.5 has been found to work well.

The outliers may be found using global statistics from all of the wafer. Alternatively, the outliers for a particular window or area of the wafer may be found using local statistics, which is a more sensitive approach. However, the tradeoff is robustness because a global approach tends to be more robust than a local approach.

As shown in FIG. 3C, portions of the Haze data that have an intensity value above a value equal to the mean $\mu$ plus $\alpha$ times the standard deviation $\sigma$ (i.e., $\mu+\alpha\sigma$) are excluded from the fitting plan, while Haze data below a value equal to the mean $\mu$ plus $\alpha$ times the standard deviation $\sigma$ are included within the fitting plan.

Figure 4:
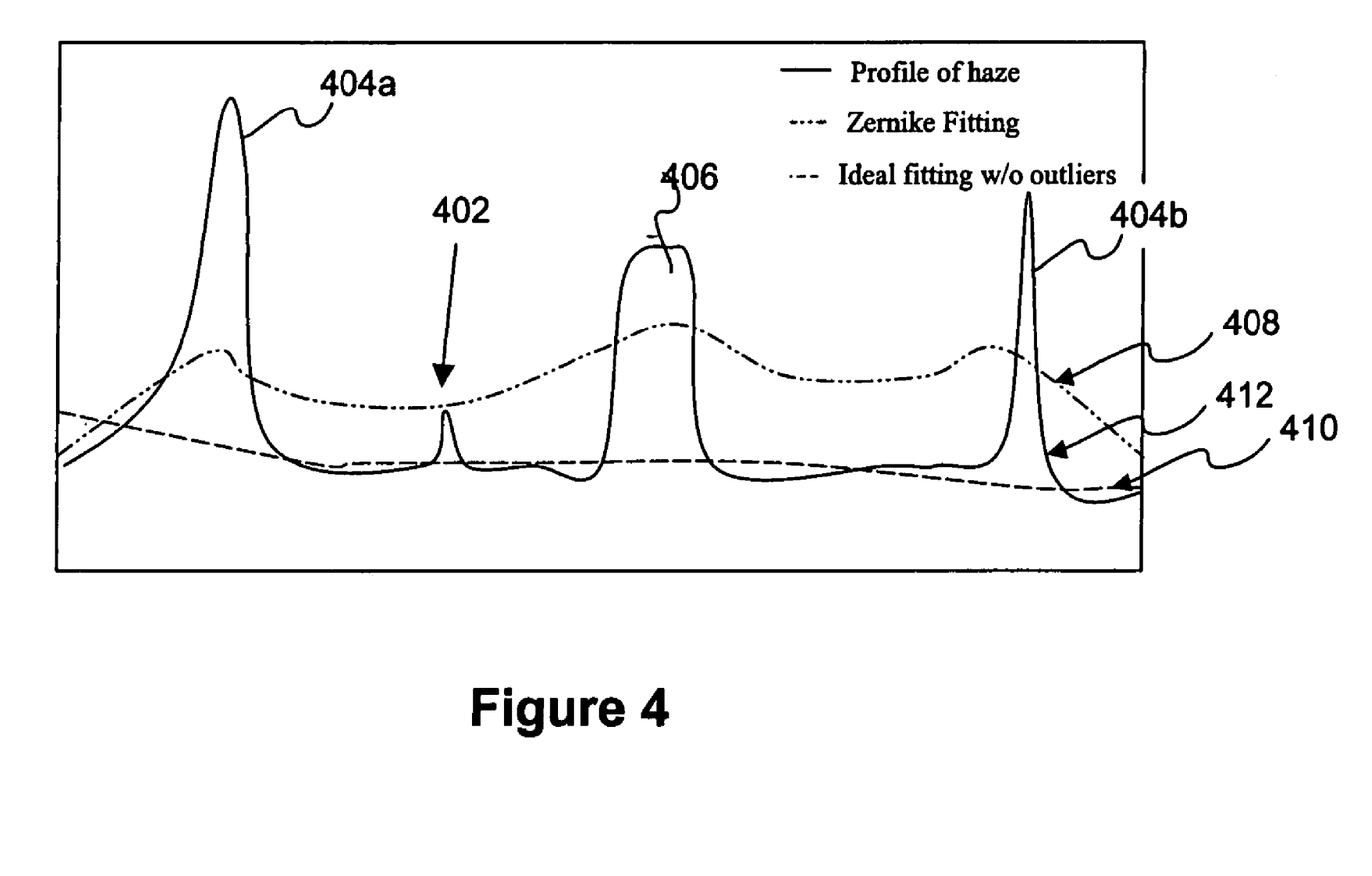
FIG. 4 is a diagrammatic representation of a Zernike fitting without excluding outliers and an ideal fitting excluding outliers as applied to a Haze data profile having a small scratch in accordance with embodiment of the present invention.

FIG. 4 is a diagrammatic representation of a Zernike fitting without excluding outliers 408 and an ideal fitting excluding outliers 410 as applied to a Haze data profile 412 having a small scratch 402 in accordance with embodiment of the present invention. As shown, the Haze data includes two wafer edges 404a and 404b, a large blob 406, and a small scratch 402. When a Zernike fitting 408 is applied to this Haze data without excluding outliers, this type of fitting will exclude scratch 402 from the residual data when the fitting 408 is subtracted from the Haze data 412 since the scratch in the Haze data 412 falls below the fitting profile 408. In contrast, a fitting 410 which excludes the wafer edges 404 and large blob 406 (and possibly the small scratch 402) will not result in excluding the small scratch 402 from the residual data when the fitting 410 is subtracted from the Haze data 412 since the scratch now rises above the fitting 410.

Figure 5A:
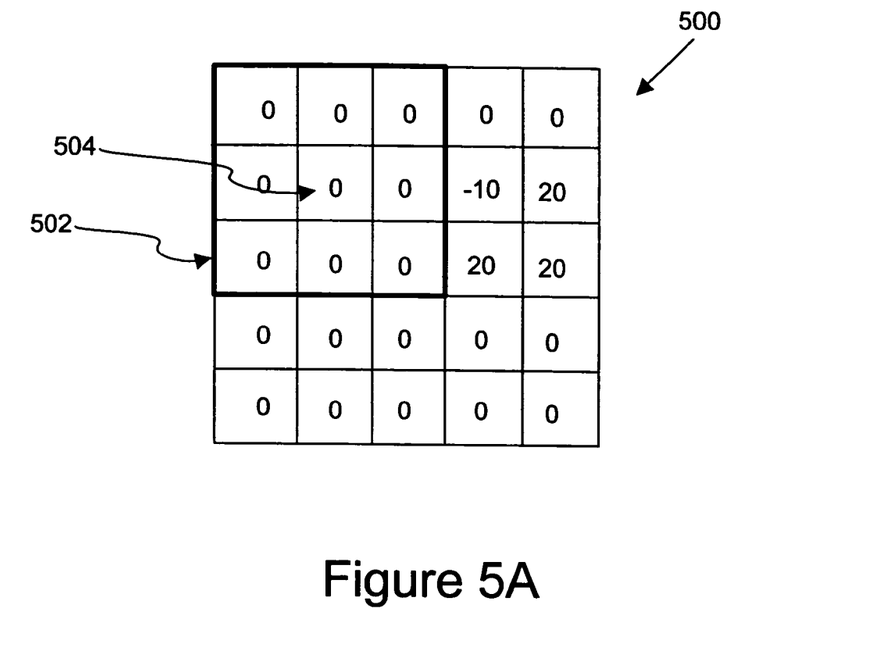
FIGS. 5A through 5B are each a diagrammatic representation of a residual image in accordance with one embodiment of the present invention.
Figure 5B:
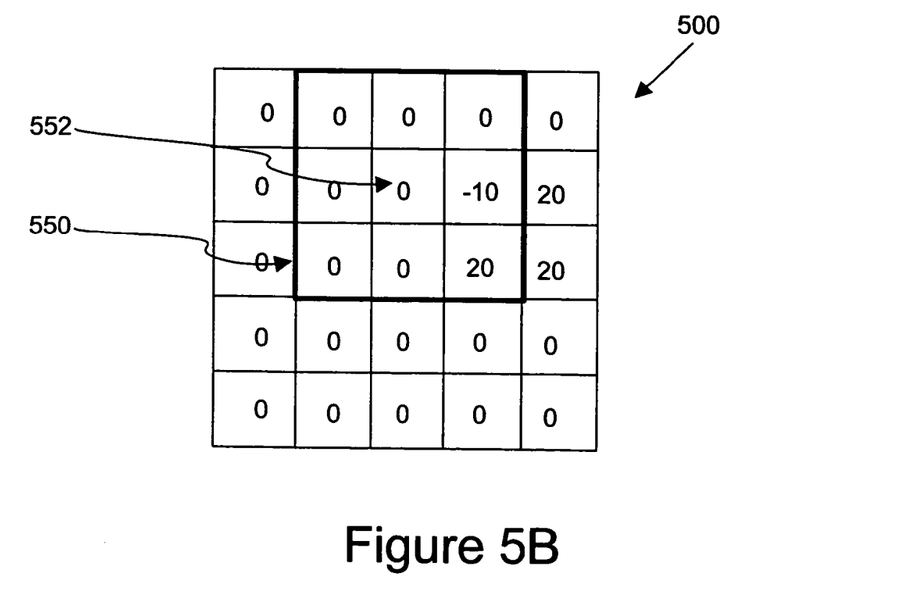

FIGS. 5A through 5B are each a diagrammatic representation of a residual image 500 in accordance with one embodiment of the present invention. These diagrams will be used to illustrate two example techniques for analyzing residual data (which has been extracted from the Haze data) to detect defects in accordance with one embodiment of the present invention. As shown, the residual image 500 is a 5×5 pixel representation of the residual data. This size is merely used to illustrate techniques of the present invention and may be sized to any suitable size or shape.

After the residual data is obtained, portions of this residual data may be analyzed window by window to determine whether a defect is present within each window. FIG. 5A shows a first window 502 having center pixel 504 within residual image 500. When this window 502 is moved to the right one pixel, window 550 having center pixel 552 results, as illustrated in FIG. 5B. In a first technique, a pixel having a minimum intensity and a pixel having a maximum intensity are determined for each window. The maximum intensity pixel value is subtracted from the minimum intensity pixel value for each window to result in a intensity difference. This intensity difference is then compared to a predetermined threshold to determine whether a defect is present for the windows central pixel. For example, if the difference intensity is greater than the predetermined threshold, it is determined that a defect is present for the central pixel.

When the first technique is applied to FIG. 5A, the maximum and minimum intensity pixel each have a value of 0 for window 502. The difference in intensity is also equal to 0 for window 502. If the predetermined threshold is equal to 10, for example, then it will be determined that window 502 and its corresponding center pixel 504 do not have a defect. In contrast, the window 550 and center pixel 552 of FIG. 5B are determined to have a defect. More specifically, the maximum pixel value is 20 and the minimum value pixel is −10 for window 550. Subtracting the minimum pixel value −10 from the maximum pixel value 20 results in a difference value of 30 for window 550. This difference intensity value of 30 is greater than the exemplary threshold of 10. Accordingly, it may be determined that center pixel 552 of window 550 has a defect.

In a second technique, the following parameters are determined for each window:

$$A = I_0 - \min(I_i)$$

$$B = \max(I_i) - I_0$$

It is then determined whether the maximum of these two parameters A and B is greater than the predetermined threshold. If the maximum of these two parameters is greater than the predetermined threshold, it is determined that the center pixel has a defect.

When the second technique is applied to FIG. 5A, the parameters A and B have a value of 0 for window 502 since all of the pixels have a 0 value. Accordingly, the maximum of A and B is 0 for window 502. When the predetermined threshold is equal to 10, for example, then it is determined that window 502 and its corresponding center pixel 504 do not have a defect since the maximum value of 0 for window 502 is less than the threshold value of 10. In contrast, window 550 and center pixel 552 of FIG. 5B are determined to have a defect. More specifically, the maximum pixel value is 20 and the minimum value pixel is −10 for window 550. The center pixel 552 has a value of 0. The A parameter then equals the center pixel value 0 minus the minimum pixel value −10, resulting in A=10 for window 550. The B parameter then equals the maximum pixel value 20 minus the center pixel value 0, resulting in B=20 for window 550. The maximum of A and B for window 550 is then equal to 20. Accordingly, it may be determined that center pixel 552 of window 550 has a defect since this maximum 20 is greater than the threshold value 10.

Figure 6:
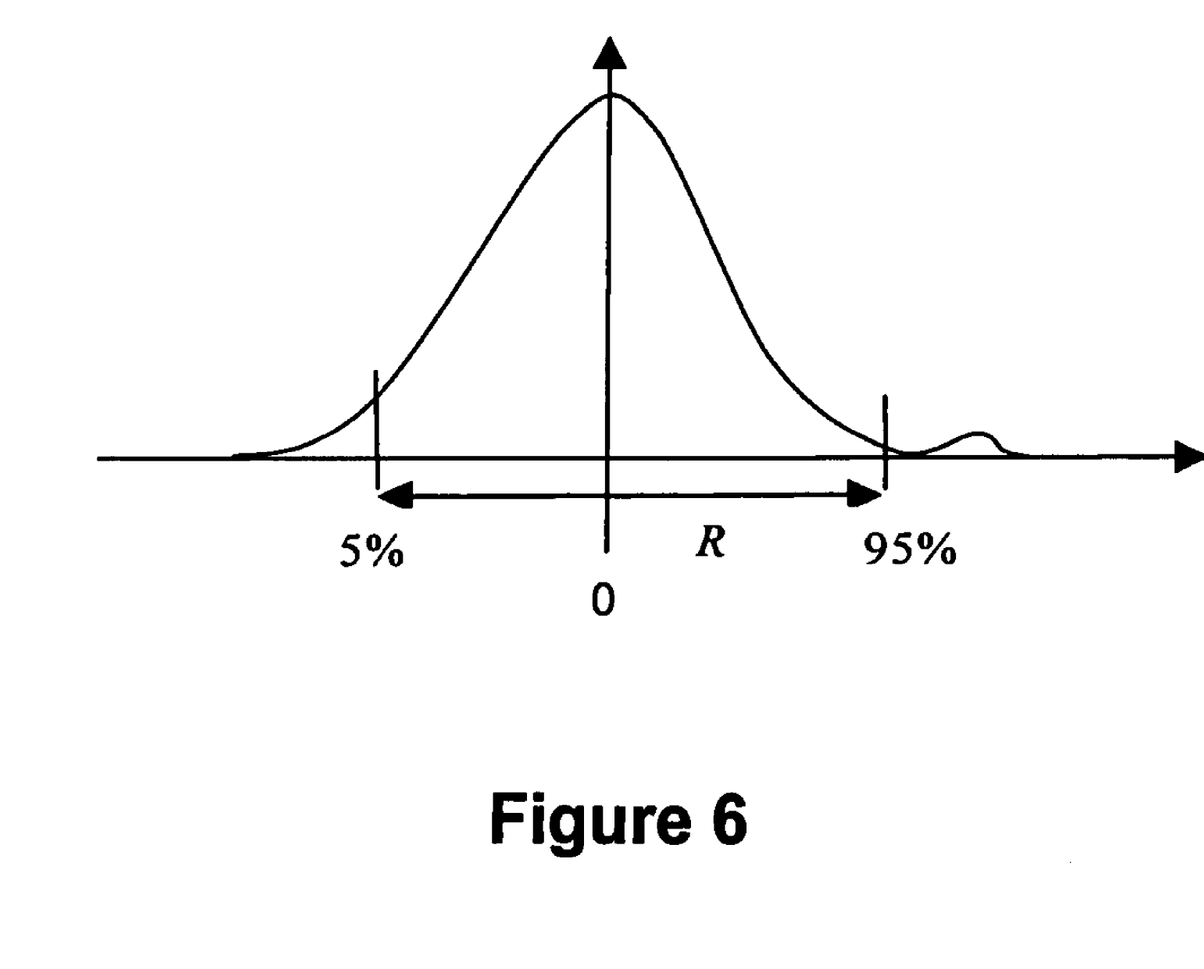
FIG. 6 shows a histogram of exemplary residual data in accordance with one embodiment of the present invention.

The predetermined threshold may be determined in any suitable manner. Since the Haze variation or the roughness of the wafer in the case of polished silicon wafers increases during the production of batches of wafers, an adaptive threshold approach is preferable utilized. In this technique, a histogram of the residual data is first determined as illustrated in FIG. 6. A range is then selected to include a significant portion of the residual data. In one embodiment, the range includes 5% to 95% of the residual intensity values. The goal is to exclude the probable defects from this range. A variable factor may then be multiplied with this range value to determine a variable threshold. In a specific embodiment, the threshold is determined by the following formula;

$$T=\alpha *R+\beta$$

The parameter α is a relative threshold factor and parameter β is a fixed or absolute threshold value. Thus, when an absolute threshold is desired, parameter α is set to zero. When a relative threshold is desired, the parameter β may be set to zero. The parameter α is then multiplied against a variable range (R) value to obtain a threshold value which depends on the range (R) of intensity values. A value of 0.5 for α seems to work well.

Figure 7:
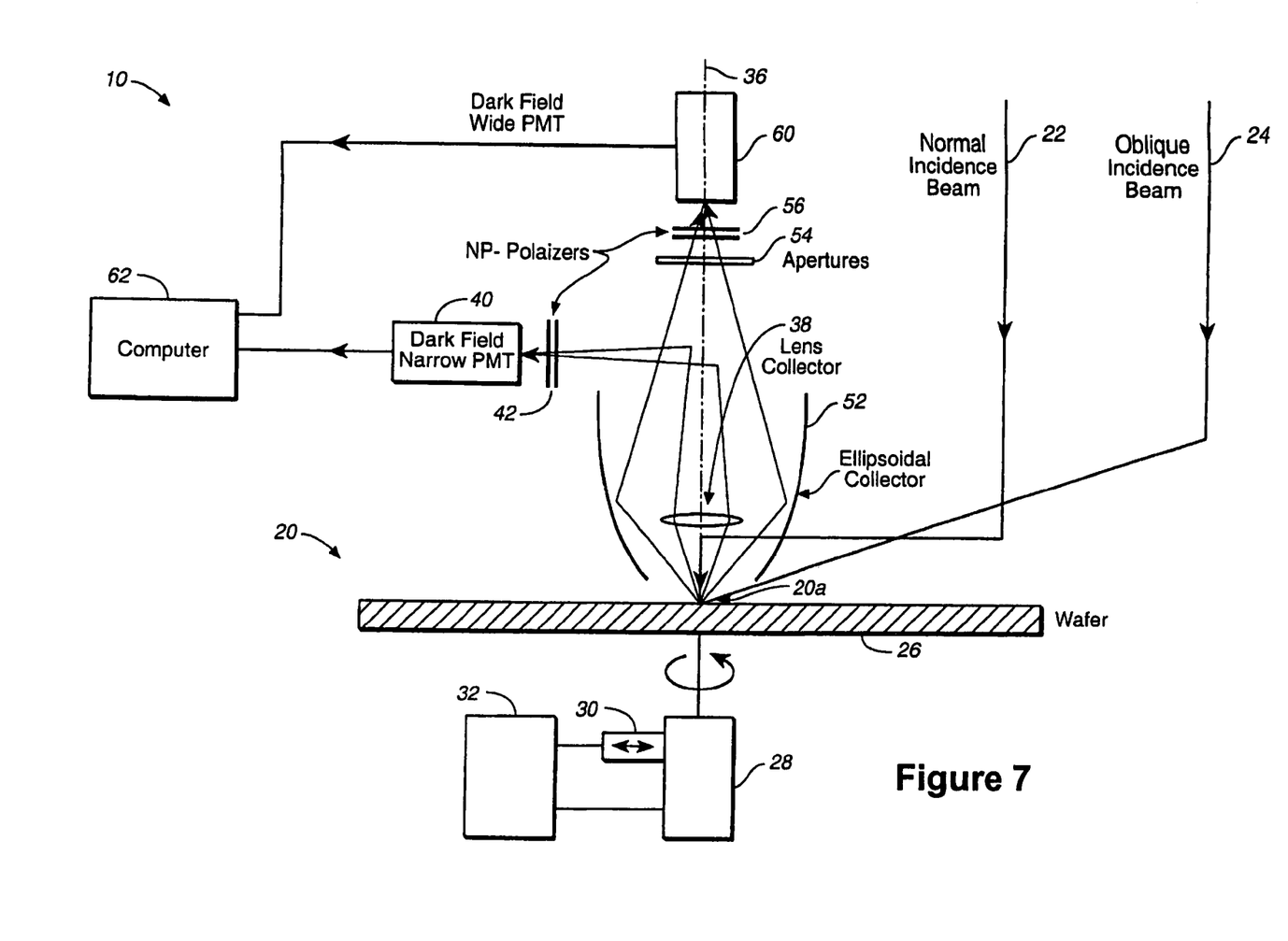
FIG. 7 is a diagrammatic representation of bare wafer inspector system in which the techniques of the present invention may be implemented.

FIG. 7 is a diagrammatic representation of bare wafer inspector system 10 in which the techniques of the present invention may be implemented. Aspects of this system 10 are described in U.S. Pat. Nos. 6,271,916 and 6,201,601, both of which are incorporated herein by reference in their entirety. To simplify the figure, some of the optical components of the system have been omitted, such as components directing the illumination beams to the wafer. The wafer 20 is illuminated by a normal incidence beam 22 and/or an oblique incidence beam 24. Wafer 20 is supported on a chuck 26 which is rotated by a motor 28 and translated in a direction by gear 30 so that beams 22 and/or 24 illuminates an area or spot 20*a* which is caused to move and trace a spiral path on the surface of wafer 20 to inspect the surface of the wafer. Motor 28 and gear 30 are controlled by controller 32 in a manner known to those skilled in the art. Alternatively, the beam(s) 22, 24 may be caused to move in a manner known to those skilled in the art to trace the spiral path or another type of scan path.

The area or spot 20*a* illuminated by either one or both-beams on wafer 20 scatters radiation from the beam(s). The radiation scattered by area 20*a* along directions close to a line 36 perpendicular to the surface of the wafer and passing through the area 20*a* is collected and focused by lens collector 38 and directed to a PMT 40.

Since lens 38 collects the scattered radiation along directions close to the normal direction, such collection channel is referred to herein as the narrow channel, and 40 as the dark field narrow collector. When desired, one or more polarizers 42 may be placed in the path of the collected radiation in the narrow channel.

Radiation scattered by spot 20*a* of wafer 20, illuminated by either one or both beams 22, 24, along directions away from the normal direction 36 is collected by an ellipsoidal collector 52 and focused through an aperture 54 and optional polarizers 56 to dark field collector 60. The outputs of detectors 40, 60 are supplied to a computer 62 for processing the signals and determining the presence of anomalies and their characteristics.

Preferably, axi-symmetrical collectors are used. In the illustrated embodiment, the wide and a narrow collector are used to collect Haze data. Since the ellipsoidal collector 52 collects scattered radiation along directions at wider angles from the normal direction 36 than lens 38, such collection channel is referred to as the wide channel or collector. Lens 38 is referred to as the narrow channel or collector. In alternative embodiments, Haze data may be obtained from a bright field channel, a phase channel, and a segmented (in angle) channel. In general, Haze data is obtained by averaging the scattered light collected within a certain XY spatial extent (and angle according to the chosen collector). The Haze data may be separated from the point defects in any suitable manner, such as a lowpass filtered version of the total scatter.

Regardless of the system's configuration, it may employ one or more memories or memory modules configured to store data, program instructions for the general-purpose inspection operations and/or the inventive techniques described herein. The program instructions may control the operation of an operating system and/or one or more applications, for example. The memory or memories may also be configured to store images of scanned specimens and position data, as well as values for particular operating parameters of the system.

Because such information and program instructions may be employed to implement the systems/methods described herein, the present invention relates to machine readable media that include program instructions, state information, etc. for performing various operations described herein. Examples of machine-readable media include, but are not limited to, magnetic media such as hard disks, floppy disks, and magnetic tape; optical media such as CD-ROM disks; magneto-optical media such as floptical disks; and hardware devices that are specially configured to store and perform program instructions, such as read-only memory devices (ROM) and random access memory (RAM). The invention may also be embodied in a carrier wave traveling over an appropriate medium such as airwaves, optical lines, electric lines, etc. Examples of program instructions include both machine code, such as produced by a compiler, and files containing higher level code that may be executed by the computer using an interpreter.

Although the foregoing invention has been described in some detail for purposes of clarity of understanding, it will be apparent that certain changes and modifications may be practiced within the scope of the appended claims. Although the techniques of the present invention has been described as being applied to bare or unpatterned samples, of course, they could also easily be applied to patterned wafers. Here, the wide collector signal is split and combined electronically to suppress the pattern noise. Therefore, the described embodiments should be taken as illustrative and not restrictive, and the invention should not be limited to the details given herein but should be defined by the following claims and their full scope of equivalents.

What is claimed is:

1. A method of analyzing Haze data provided from a surface of a specimen, the method comprising:
   providing Haze data which corresponds to a surface roughness of the specimen; and removing low frequency variations from the Haze data to form residual data that corresponds to any defects which are present in the surface of the specimen, wherein the specimen is selected from a group consisting of a bare semiconductor specimen and a semiconductor specimen having one or more substantially uniform film layer(s) disposed thereon, wherein removing low frequency variations from the Haze data is accomplished by:

fitting the low frequency variations of the Haze data to a fitting plan; and subtracting the fitting plan from the Haze data to form the residual data, wherein the fitting plan is in the form of a two dimensional (2D) polynomial equation.

2. A method as recited in claim 1, wherein the 2D polynomial equation is a Zernike polynomial.

3. A method as recited in claim 2, wherein the Zernike polynomial is expressed in terms of a normalized radius r of a pupil and an azimuthal angle $\phi$.

4. A method as recited in claim 3, wherein the Zernike polynomial includes terms for tilt direction, tilt magnitude, and bowl shape.

5. A method as recited in claim 4, wherein the Zernike polynomial has an order greater than 2.

6. A method as recited in claim 3, wherein the Zernike polynomial has an order less than 9.

7. A method as recited in claim 1, further comprising pre-processing the Haze data to exclude a portion of the Haze data from the fitting plan.

8. A method as recited in claim 7, wherein the pre-processing includes excluding outliers within the Haze data from the fitting plan.

9. A method as recited in claim 8, wherein the outliers include intensity values which correspond to the specimen's edge and large blob defects and imperfections which create large absolute intensity values as well as high local haze gradients.

10. A method as recited in claim 8, wherein excluding outliers comprises:

determining a mean and standard deviation for the Haze data;

determining a threshold which depends on the mean and standard deviation; and excluding Haze data which falls below the threshold from the fitting plan.

11. A method as recited in claim 10, wherein the threshold is set equal to the mean plus a predetermined factor multiplied by the standard deviation.

12. A method as recited in claim 11, wherein the predetermined factor is set equal to 1.5.

13. A method as recited in claim 11, further comprising determining the predetermined factor experimentally.

14. A method as recited in claim 1, further comprising analyzing the residual data to determine whether the specimen has any defects.

15. A method as recited in claim 14, wherein the residual data is analyzed by:

a) obtaining a window which contains a portion of the residual data;

b) determining a minimum pixel having a lowest intensity and a maximum pixel having a maximum intensity within the obtained window; and c) determining whether the window has a defect based on the minimum pixel, the maximum pixel, and a predetermined threshold.

16. A method as recited in claim 15, wherein when the minimum pixel minus the maximum pixel is greater than the predetermined threshold, it is determined that the window has a defect.

17. A method as recited in claim 16, further comprising repeating steps (a) through (c) for a plurality of windows which contain other areas of the residual data so that all portions of the residual data are analyzed.

18. A method as recited in claim 15, wherein when a maximum of (A) a center pixel of the window minus the minimum pixel and (B) the maximum pixel minus the center pixel is greater than the predetermined threshold, it is determined that the window has a defect.

19. A method as recited in claim 18, further comprising repeating steps (a) through (c) for a plurality of windows which contain other areas of the residual data so that all portions of the residual data are analyzed.

20. A method as recited in claim 15, wherein the predetermined threshold is determined by:

determining a histogram based on the residual data;

selecting a range of residual values front the residual data; and determining a threshold based on the selected range.

21. A method as recited in claim 20, wherein the threshold is determined by multiplying a predetermined factor times the range, wherein the predetermined factor varies for each system which provides Haze data so that the threshold is normalized between the different systems.

22. A method as recited in claim 21, wherein the threshold is determined by multiplying a factor times the range plus an absolute threshold value.

23. A method as recited in claim 22, further comprising setting the predetermined factor to zero when the absolute threshold is desired.

24. A method as recited in claim 23, further comprising setting the absolute threshold to zero when a relative threshold is desired.

25. A method as recited in claim 21, wherein the predetermined factor is 0.5.

26. A method as recited in claim 20, wherein the selected range is between about 5 and 95 percent.

27. A method as recited in claim 1, wherein removing low frequency variations from the Haze data is accomplished using a filter.

28. A method as recited in claim 1, wherein the specimen comprises a semiconductor substrate having one or more unpatterned films thereon.

29. A method as recited in claim 1, wherein the low frequency variations include any combination of the following: a uniform roughness of the specimen surface, an angled plane of the specimen surface, and a higher order roughness variations of the specimen surface.

30. A computer system operable to analyze Haze data provided from a surface of a specimen, the computer system comprising:

one or more processors;

one or more memory, wherein at least one of the processors and memory are adapted for;

providing Haze data which corresponds to a surface roughness of the specimen; and removing low frequency variations from the Haze data form residual data that corresponds to any defects which are present in the surface of the specimen, wherein the specimen is selected from a group consisting of a bare semiconductor specimen and a semiconductor specimen having one or more substantially uniform film layer(s) disposed thereon, wherein removing low frequency variation from the Haze data is accomplished by:
fitting the low frequency variations of the Haze data to a fitting plan; and
subtracting the fitting plan from the Haze data to form the residual data, and
wherein the fitting plan is in the form of a two dimensional (2D) polynomial equation.

31. A computer system as recited in claim 30, wherein the 2D polynomial equation is a Zernike polynomial.

32. A computer system as recited in claim 31, wherein the Zernike polynomial has an order greater than 2.

33. A computer system as recited in claim 31, wherein the Zernike polynomial has an order less than 9.

34. A computer system as recited in claim 30, further comprising pre-processing the Haze data to exclude a portion of the Haze data from the fitting plan.

35. A computer system as recited in claim 34, wherein the pre-processing includes excluding outliers within the Haze data from the fitting plan.

36. A computer system as recited in claim 35, wherein the outliers include intensity values which correspond to the specimen's edge and large blob defects.

37. A computer system as recited in claim 35, wherein excluding outliers comprises:
determining a mean and standard deviation for the Haze data;
determining a threshold which depends on the mean and standard deviation; and
excluding Haze data which falls below the threshold from the fitting plan.

38. A computer system as recited in claim 30, wherein at least one of the processors and memory are further adapted for analyzing the residual data to determine whether the specimen has any defects.

39. A computer system as recited in claim 38, wherein the residual data is analyzed by:
a) obtaining a window which contains a portion of the residual data;
b) determining a minimum pixel having a lowest intensity and a maximum pixel having a maximum intensity within the obtained window; and
c) determining whether the window has a defect based on the minimum pixel, the maximum pixel, and a predetermined threshold.

40. A computer system as recited in claim 39, wherein when the minimum pixel minus the maximum pixel is greater than the predetermined threshold, it is determined that the window has a defect.

41. A computer system as recited in claim 39, wherein when a maximum of (A) a center pixel of the window minus the minimum pixel and (B) the maximum pixel minus the center pixel is greater than the predetermined threshold, it is determined that the window has a defect.

42. A computer system as recited in claim 39, wherein the predetermined threshold is determined by:
determining a histogram based on the residual data;
selecting a range of residual values from the residual data; and
determining a threshold based on the selected range.

43. A computer system as recited in claim 42, wherein to threshold is determined by multiplying a predetermined factor times the selected range, wherein the predetermined factor varies for each system which provides Haze data so that the threshold is normalized between the different systems.

44. A computer system as recited in claim 43, wherein the predetermined factor is 0.5.

45. A computer system as recited in claim 42, wherein the selected range is between about 5 and 95 percent.

46. A computer system as recited in claim 30, wherein removing low frequency variations from the Haze data is accomplished using a filter.

47. A computer program product for analyzing Haze data provided from a surface of a specimen, the computer program product, comprising:
at least one computer readable medium;
computer program instructions stored within the at least one computer readable product configured to:
providing Haze data which corresponds to a surface roughness of the specimen; and
removing low frequency variations from the Haze data to form residual data that corresponds to any defects which present in the surface of the specimen, wherein the specimen is selected from a group consisting of a bare semiconductor specimen and a semiconductor specimen having one or more substantially uniform film layer(s) disposed thereon,
wherein removing low frequency variations from the Haze data is accomplished by:
fitting the low frequency variations of the Haze data to a fitting plan; and
subtracting the fitting plan from the Haze data to form the residual data, and
wherein the fitting plan is in the form of a two dimensional (2D) polynomial equation.

48. A computer program product as recited in claim 47, wherein the 2D polynomial equation is a Zernike polynomial.

49. A computer program product as recited in claim 47, further comprising pre-processing the Haze data so as to exclude outliers within the Haze data from the fitting plan.

50. A computer program product as recited in claim 49, wherein excluding outliers comprises:
determining a mean and standard deviation for the Haze data;
determining a threshold which depends on the mean and standard deviation; and
excluding Haze data which falls below the threshold from the fitting plan.

51. A computer program product as recited in claim 47, wherein the computer program instructions stored within the at least one computer readable product are further configured to analyze the residual data to determine whether the specimen has any defects.

52. A computer program product as recited in claim 51, wherein the residual data is analyzed by:
a) obtaining a window which contains a portion of the residual data;
b) determining a minimum pixel having a lowest intensity and a maximum pixel having a maximum intensity within the obtained window; and
c) determining whether the window has a defect based on the minimum pixel, the maximum pixel, and a predetermined threshold.

53. A computer program product as recited in claim 52, wherein when the minimum pixel minus to maximum pixel is greater than the predetermined threshold, it is determined that the window has a defect.

54. A computer program product as recited in claim 52, wherein when a maximum of (A) a center pixel of to window minus the minimum pixel and (B) the maximum pixel minus the center pixel is greater tan the predetermined threshold, it is determined that the window has a defect.

55. A computer program product as recited in claim 52, wherein to predetermined threshold is determined by:
   determining a histogram based on the residual data;
   selecting a range of residual values from the residual data; and
   determining a threshold based on the selected range.

56. A computer program product as recited in claim 55, wherein the threshold is determined by multiplying a predetermined factor times to selected range, wherein the predetermined factor varies for each system which provides Haze data so that the threshold is normalized between the different systems.

57. A computer program product as recited in claim 52, wherein the selected range is between about 5 and 95 percent.

58. A computer program product as recited in claim 47, wherein removing low frequency variations from the Haze data is accomplished using a filter.

* * * * *

UNITED STATES PATENT AND TRADEMARK OFFICE
CERTIFICATE OF CORRECTION

PATENT NO.        : 7,038,773 B2                                Page 1 of 1
APPLICATION NO.   : 10/848631
DATED             : May 2, 2006
INVENTOR(S)       : Kuhlmann et al.

It is certified that error appears in the above-identified patent and that said Letters Patent is hereby corrected as shown below:

In the Claims:

In line 5 of claim 20 (column 12, line 21) change "values front" to --values from--.

In line 10 of claim 30 (column 12, line 62) add --to-- before "form".

In line 16 of claim 30 (column 13, line 1) change "variation" to --variations--.

In line 1 of claim 43 (column 13, line 62) change "wherein to" to --wherein the--.

In line 11 of claim 47 (column 14, line 18) add --are-- after "which".

In line 2 of claim 53 (column 14, line 62) change "minus to" to --minus the--.

In line 2 of claim 54 (column 14, line 66) change "of to" to --of the--.

In line 4 of claim 54 (column 15, line 1) change "greater tan" to --greater than--.

In line 2 of claim 55 (column 15, line 4) change "wherein to" to --wherein the--.

In line 3 of claim 56 (column 15, line 11) change "to selected" to --the selected--.

In line 1 of claim 57 (column 16, line 4) change "claim 52" to --claim 55--.

Signed and Sealed this

Sixth Day of February, 2007

JON W. DUDAS
*Director of the United States Patent and Trademark Office*